United States Patent
Lauer et al.

(10) Patent No.: US 10,744,275 B2
(45) Date of Patent: Aug. 18, 2020

(54) MEDICAL HEAT EXCHANGER FOR HEATING MEDICAL FLUIDS BY MEANS OF A LIGHT EMITTER AND MEDICAL FLUID TREATMENT DEVICE HAVING A LIGHT EMITTER

(71) Applicant: Fresenius Medical Care Deutschland GmbH, Bad Homburg (DE)

(72) Inventors: Martin Lauer, St. Wendel (DE); Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 650 days.

(21) Appl. No.: 14/889,882

(22) PCT Filed: Jun. 18, 2014

(86) PCT No.: PCT/EP2014/062838
§ 371 (c)(1),
(2) Date: Nov. 9, 2015

(87) PCT Pub. No.: WO2014/202674
PCT Pub. Date: Dec. 24, 2014

(65) Prior Publication Data
US 2016/0082200 A1    Mar. 24, 2016

(30) Foreign Application Priority Data
Jun. 18, 2013  (DE) .................. 10 2013 010 106

(51) Int. Cl.
*A61M 5/44* (2006.01)
*A61M 1/16* (2006.01)
(Continued)

(52) U.S. Cl.
CPC .................. *A61M 5/44* (2013.01); *A61M 1/14* (2013.01); *A61M 1/1629* (2014.02);
(Continued)

(58) Field of Classification Search
CPC .................. A61M 5/44; A61M 1/1629; A61M 2205/366; A61M 2205/368;
(Continued)

(56) References Cited

U.S. PATENT DOCUMENTS

| | | | |
|---|---|---|---|
| 5,431,149 A * | 7/1995 | Fossum ..................... | F24J 2/265 126/659 |
| 2003/0135250 A1 * | 7/2003 | Lauman ................... | A61M 5/44 607/104 |

(Continued)

FOREIGN PATENT DOCUMENTS

| | | |
|---|---|---|
| DE | 102010002895 | 9/2011 |
| EP | 2311514 | 4/2011 |
| WO | WO 03/061740 | 7/2003 |

*Primary Examiner* — Nathan R Price
*Assistant Examiner* — Justin L Zamory
(74) *Attorney, Agent, or Firm* — Jacobson Holman, PLLC.

(57) ABSTRACT

The present invention proposes a medical heat exchanger for heating with a light emitter. The heat exchanger disclosed here has at least one fluid chamber having at least one outside wall which forms the fluid chamber with a fluid-tight seal, such that the fluid chamber is configured for receiving and/or conducting the medical fluid and such that the fluid chamber has at least one component, which is configured as a light absorber and is arranged within the fluid chamber in at least some sections so that there is direct contact between the component configured as the light absorber and the medical fluid in at least some sections when receiving and/or conducting the medical fluid and wherein the outside wall of the fluid chamber has at least one light-transmitting section, so that the light emitted by the light emitter can heat the
(Continued)

absorber without any local temperature peaks on the medical heat exchanger.

24 Claims, 2 Drawing Sheets

(51) Int. Cl.
*F24H 1/10* (2006.01)
*A61M 1/14* (2006.01)

(52) U.S. Cl.
CPC ... *A61M 2205/12* (2013.01); *A61M 2205/127* (2013.01); *A61M 2205/36* (2013.01); *A61M 2205/368* (2013.01); *F24H 1/101* (2013.01)

(58) Field of Classification Search
CPC .. A61M 2205/127; F24H 1/121; F24H 1/101; H05B 3/78; H05B 3/0052; Y10S 165/539
See application file for complete search history.

(56) References Cited

U.S. PATENT DOCUMENTS

2007/0235021 A1   10/2007   Reed et al.
2009/0299271 A1   12/2009   Zhang et al.

\* cited by examiner

MEDICAL HEAT EXCHANGER FOR HEATING MEDICAL FLUIDS BY MEANS OF A LIGHT EMITTER AND MEDICAL FLUID TREATMENT DEVICE HAVING A LIGHT EMITTER

TECHNICAL FIELD

The invention relates to a medical heat exchanger for heating medical fluids by means of a light emitter and to the medical fluid treatment device having a light emitter.

There are numerous problems in medical technology in which a medical fluid is to be heated to avoid cooling a patient due to the medical fluid, for example, and/or to set a preselected temperature of the medical fluid so that it is approximately the same as the patient's body temperature. Examples of such medical situations include heating of blood in an extracorporeal blood circulation or heating of dialysis fluid in a dialysis fluid circulation or heating of a replacement fluid, such as that which occurs in hemodialysis, hemofiltration and hemodiafiltration. In blood treatment methods using an extracorporeal blood circulation, blood is withdrawn from the patient via an arterial dialysis needle from a vascular access with a fistula or shunt, then this blood passes from the arterial dialysis needle through an arterial tubing line to a blood treatment unit, for example, a dialyzer or filter by means of a pump, for example, and then after flowing through the blood treatment unit it is sent via a venous tubing line back into the fistula or the shunt of the patient. The blood may cool off substantially in the extracorporeal blood circulation due to heat losses to the surroundings. The blood can be heated back to a predetermined temperature by means of a medical heat exchanger before the blood is returned to the patient. A medical heat exchanger suitable for this purpose may be arranged in or on the venous tubing line. There are known medical heat exchangers in which a line section of the venous line is coiled around an electric heating drum.

Additional examples of the use of a medical heat exchanger include the heating of dialysis fluid in peritoneal dialysis or the heating of infusion solutions in Infusion technology.

BACKGROUND

The heating of a medical fluid by means of a medical heat exchanger can be accomplished by electric resistance heating elements such as heating plates or by means of electric emitters for light which heat the medical heat exchanger indirectly from the outside.

The document WO 03/061740 A1 describes a medical heat exchanger which is embodied as a disposable heating cassette, such that the heating of the heating cassette takes place from the outside on the one hand by means of an electric light emitter which is coupled to the heating cassette and on the other hand additionally with an electric resistance heating plate coupled to the heating cassette on the opposite side of the heating cassette. In an alternative embodiment, the electric heating plate also has, in addition to the heating cassette, an absorber for infrared radiation which additionally heats the heating cassette from the outside.

The generic medical heat exchangers known from the prior art have considerable disadvantages because the coupling surface of the light emitter on the machine side and the coupling surface of the disposable heating cassette are subject to high thermal loads so that the maximum temperatures that occur must not exceed 80° C., for example, for safety reasons as well as factors pertaining to the materials. Therefore this requires at least large coupling surfaces and a mechanically complex coupling of the disposable heating cassette to the coupling surface of the light emitter on the machine side. Furthermore, suction removal of the air trapped between the coupling surface of the disposable heating cassette and the coupling surface of the light emitter on the machine side may be necessary during coupling. If the coupling surface of the disposable heating cassette is designed as a film, then a complex pressing of the film to the coupling surface of light emitter may be necessary in combination with the suction removal of air. Despite such complex measures, a substantial portion of the radiation of the light emitter must nevertheless be dissipated through component cooling on the machine side and is therefore not available for heating the medical fluid.

When light passes through a material, some of the light is converted into heat and some of the light is allowed to pass through.

Within a very small layer thickness dx of the material, the radiation intensity of the light is reduced by the same fraction, which is described by the absorption coefficients. The absorption coefficient is a substance-specific function, which depends on the wavelength $\lambda$ of the light; this is referred to as the absorption spectrum $\mu(\lambda)$ of the substance. The higher the absorption coefficient at a certain wavelength, the greater is the absorbed radiation intensity of light of a certain wavelength, which is converted into heat in the very small layer dx.

Similarly, the transmission coefficient describes the passage of light through a very small layer thickness dx of the material. The transmission coefficient is similarly a specific function of the wavelength $\lambda$ of the light which is referred to as the transmission spectrum $\mu(\lambda)$ of the substance. The greater the transmission coefficient at a certain wavelength, the greater is the radiation intensity of the light of a certain wavelength passing through the very small layer dx.

The absorbance $\alpha$ of a body is defined as the quotient of the absorbed radiation energy and the radiation energy that occurs. The absorbance is therefore a measure for characterizing a body with regard to its property of converting incident light into heat.

The transmittance $\tau$ of a body is defined as the quotient of the radiation energy allowed to pass through and the resulting radiation energy.

Bodies which absorb all the radiation energy and convert it completely into heat have an absorbance of 1 and a transmittance of 0 ("absolute black bodies").

The reflectance $\rho$ of a body is defined as the quotient of the reflected radiant energy and the incoming radiant energy.

It holds that: transmittance $\tau$+absorbance $\alpha$+reflectance $\rho$=1 Bodies that reflect all of the incident radiation or allow all of the incident radiation to pass through have an absorbance of 0.

A known advantage of the generic medical heat exchangers heated by a light emitter is the good electric safety because of the spatial distance between the light emitter and the fluid.

A known problem of the generic medical heat exchangers which are heated by a light emitter is the at least local occurrence of inadmissible temperature peaks; this problem occurs in particular with medical heat exchangers made of materials having a low thermal conductivity. As a result of the low thermal conductivity, such medical heat exchangers deliver a substantial portion of the incident heat to the air surrounding the medical heat exchanger, which has a negative effect on the efficiency in heat transfer.

It is known that medical heat exchangers can be produced as disposable heating cassettes (disposable items). For cost reasons, the most inexpensive possible plastics are used for this purpose but they usually have the disadvantage described above of a low thermal conductivity.

Local temperature peaks on the medical heat exchanger may, on the one hand, damage the materials of the medical heat exchanger or may even destroy them due to heating, melting or fire. On the other hand, such local temperature peaks can also damage the medical fluid, but this must be prevented from the standpoint of patient safety in particular. Not least of all, the light emitter may also overheat.

Known structural measures to prevent the at least local occurrence of inadmissible temperature peaks is the use of large heat exchanger surface areas as well as the targeted deflection of radiation and radiation shielding, each of which entails high costs and a reduced efficiency in heat transfer.

One object of the present invention is therefore to provide an improved medical heat exchanger.

SUMMARY

This object is achieved with the independent patent claims 1, 15, 16 and 17. Advantageous embodiments are the subject matter of the dependent claims. The advantages of the medical heat exchanger according to claim 1 can be achieved undiminished with a medical tubing set according to claim 15 or with a medical fluid treatment device according to claim 16 or according to claim 17.

Medical fluids in the sense of the present invention include, for example, fluids from the group of blood, blood plasma, dialysis fluid, replacement fluid, physiological saline solution, medication solution, contrast medium, infusion solution, peritoneal dialysis solution as well as mixtures of such fluids with which those skilled in the art are familiar but they are not limited to these examples. Examples of mixtures of such fluids include, e.g., blood mixed with replacement fluid and/or physiological saline solution and/or medication solution and/or contrast medium and/or infusion solution.

According to a first aspect, the medical heat exchanger has at least one fluid chamber having at least one outside wall which forms the fluid chamber with a fluid seal, such that the fluid chamber is configured for receiving the medical fluid and/or for passing it through and such that the fluid chamber has at least one component which is configured as a light absorber arranged within the fluid chamber in at least some sections, such that there is direct contact between the medical fluid and the component configured as a light absorber in at least some sections while receiving the medical fluid and/or passing it through.

A component configured as a light absorber in accordance with the present teaching is understood to be a component that is provided and suitable for absorbing a predominant portion of the incident light.

According to another aspect, the component configured as a light absorber has a light absorbance $\alpha_2$ and a light transmittance $\tau_2$, such that the light absorbance $\alpha_2$ is preferably much greater than the light transmittance $\tau_2$ in the wavelength range of light from 200 nm to 3000 nm and especially preferably in the wavelength range of light from 350 nm to 2000 nm.

According to another aspect, the component configured as a light absorber is manufactured from a material whose absorption spectrum preferably has at least one local maximum or an absolute maximum of the absorption coefficient in the wavelength range of light from 200 nm to 3000 nm and especially preferably in the wavelength range of light from 350 nm to 2000 nm.

Heat transfer from the component configured as a light absorber to the medical fluid requires adequate heat conduction. If radiation is absorbed at a low depth of penetration, then a thermal conductivity of 0.15 W/mK for plastics, for example, is sufficient to transfer heat to the medical fluid.

According to another aspect, the component configured as a light absorber may be arranged for direct contact with the medical fluid on one side or both or all sides in the fluid chamber, i.e., the direct contact may take place by having the medical fluid flow over or around the component configured as a light absorber. A bilateral flow or all-round flow of the medical fluid around the component configured as a light absorber is especially advantageous.

The component configured as a light absorber may have a three-dimensional structure for the purpose of increasing the surface area in order to improve the heat transfer. For example, the three-dimensional structure may be embodied as ribs or webs. To improve the heat transfer from the component configured as an absorber to the medical fluid, such ribs or webs of the component configured as a light absorber may also be provided to force a repeated meandering flow deflection of the medical fluid in cooperation with opposing ribs or webs on the inside of the outside wall of the medical heat exchanger. In addition the three-dimensional structure may be designed to create a turbulent flow in order to further improve the heat transfer.

The component configured as a light absorber may have three-dimensional guide structures on its surface for generating a rotational flow so that the component configured as a light absorber has the medical fluid flowing around it, for example, in a helical rotating flow.

The component configured as a light absorber may be black or dark for visible light.

The component configured as a light absorber may be configured through a suitable choice of material for absorption of light in a broad spectrum of the wavelength or it may be configured through a suitable different choice of materials for selective absorption of light of a narrow wavelength spectrum.

For example, ceramics or metal or plastics or some other material having a sufficiently high thermal conductivity may be selected as the material for the component configured as a light absorber. In exposure to light, an essentially homogeneous temperature distribution can be achieved in the component configured as a light absorber through a sufficiently high thermal conductivity, so that temperature peaks are prevented and the medical fluid is homogenously heated.

The component configured as a light absorber may be manufactured from a compounded material, in particular from a compounded thermoplastic injectable plastic or from a compounded thermoplastic extrudable plastic or from an injection-molded part coated by metal vapor or an extrusion part coated by metal vapor or it may be made of a metal, in particular stainless steel, or a ceramic material, in particular $Al_2O_3$ or AlN.

The component configured as a light absorber may be made of a compounded thermoplastic material having metallic and/or ceramic and/or oxidic filling materials, or the component configured as a light absorber may be made of a thermoplastic material having inserted layers of these filling materials.

According to another aspect, the fluid chamber may have at least one Inlet in the outside wall of the fluid chamber for supplying the medical fluid to the fluid chamber and/or at least one outlet in the outside wall of the fluid chamber for removing the at least one medical fluid from the fluid chamber.

According to another aspect, the fluid chamber may have a port and/or a septum for supplying and/or removing the medical fluid.

The fluid chamber may be designed to be essentially rigid in sections or as a whole or may be designed to be flexible in sections or as a whole. The fluid chamber may be manufactured in one piece or may be assembled from at least two pieces with a fluid-tight seal. One example of a fluid chamber designed to be rigid in sections is a fluid cassette manufactured by injection molding or thermoforming with an essentially rigid hard part having cavities and/or channels for conveying the medical fluid, such that the cavities and/or channels are covered with a flexible film and form an interior of the fluid channel and the hard part and the flexible film together form the outside wall of the fluid channel.

An example of a fluid chamber designed to be essentially rigid on the whole may be composed of two injection-molded parts, at least one of which has a cavity, for example, an essentially rigid first housing part and an essentially rigid second housing part, such that the two parts are or can be joined together with a fluid-tight seal, so that the at least one cavity forms an interior of the fluid chamber and the first housing part together with the second housing part forms the outside wall of the fluid chamber.

An example of a fluid chamber having a flexible design on the whole is a fluid bag. The outside wall of the fluid chamber is formed by two flexible film sections. The component configured as a light absorber is a black film in this exemplary embodiment which is welded in at least some sections between the two flexible films of the outside wall.

According to another aspect, the heat exchanger has at least one section of the outside wall of the fluid chamber configured as a light-transmitting section.

According to another aspect the heat exchanger is manufactured in one part by injection blow-molding from at least one thermoplastic material.

In accordance with the present teaching, a section of the outside wall of the fluid chamber configured as a light-transmitting section is understood to be a component which is provided and is suitable for allowing most of the incident light to pass through and only a small portion of the incident light to be reflected or absorbed. Thus the section configured as a light-transmitting section heats up only slightly with incident light and incident light is allowed to pass through with a high efficiency.

Therefore temperature peaks on the outside wall of the fluid chamber are prevented because the wall hardly heats up at all.

According to another aspect, the section of the outside wall of the fluid chamber configured as a light-transmitting section has an absorbance $\alpha_1$ for light and a transmittance $\tau_1$ for light, such that the light transmittance $\tau_1$ is preferably much greater than the light absorbance $\alpha_1$ in the wavelength range of light from 200 nm to 3000 nm and especially preferably in the wavelength range of light from 350 nm to 2000 nm.

According to another aspect, the section of the outside wall of the fluid chamber configured as a light-transmitting section is made of a material whose transmission spectrum preferably has at least one local maximum or one absolute maximum of the transmission coefficient in the wavelength range of light from 200 nm to 3000 nm and especially preferably in the wavelength range of light from 350 nm to 2000 nm.

The section of the outside wall of the fluid chamber configured as a light-transmitting section may be designed to be at least translucent or even transparent for visible light.

The section of the outside wall configured as a light-transmitting section may extend over a portion of the outside wall or essentially over the entire outside wall. Therefore temperature peaks due to the incident light on the outside wall of the fluid chamber are advantageously prevented.

The section of the outside wall configured as a light-transmitting section may consist of an opening having a peripheral fluid-tight frame into which a transparent panel is inserted. The panel may be made of glass, quartz glass or polyacrylic, for example. The panel may be essentially round or essentially rectangular.

According to another aspect, the medical heat exchanger may be part of a medical tubing set wherein the medical tubing set may additionally have other components with which those skilled in the art are familiar.

According to another aspect, the medical heat exchanger may be an integral component of a medical fluid treatment device, such that the fluid treatment device has at least one light emitter for heating the medical heat exchanger.

One example of such an embodiment is a hemodialysis machine having a dialysis fluid circulation and a source for replacement fluid, wherein the dialysis fluid and/or the replacement fluid is heated by means of a medical heat exchanger according to the invention, as installed in the dialysis machine. In such an embodiment, the medical heat exchanger is typically replaced by a qualified service technician and is intended for long-term use.

According to another aspect, the medical heat exchanger may be configured for coupling to a medical fluid treatment device, the medical fluid treatment device having at least one light emitter and at least one coupling surface for the medical heat exchanger, said coupling surface being configured as a light-transmitting section.

One example of such an embodiment is a hemodialysis machine in which the blood in an extracorporeal blood circulation is to be heated by means of a heat exchanger according to the present disclosure. In such an embodiment the medical heat exchanger is coupled by the user of the hemodialysis machine to the coupling surface of the hemodialysis machine as a new disposable product before the start of each blood treatment.

According to another aspect the medical fluid treatment device has a control and/or regulating unit with a controller configured for controlling and/or regulating the radiation power of the at least one light emitter. The control and/or regulating unit with the controller may have a signal connection to a temperature-measuring device in or on the fluid line, preferably on the fluid outlet of the medical heat exchanger.

The temperature-measuring device may be part of the fluid treatment device wherein the measurement site of the fluid line is inserted into a corresponding measurement receptacle on the fluid treatment device.

The light emitter may be configured for emitting light in a broad spectrum of the wavelength, for example, comprising the visible light or comprising the visible light and the infrared light.

Alternatively, the light emitter may be configured for selective emission of light in a narrow wavelength spectrum.

The light emitter is especially advantageously configured for selective emission of a spectrum of light in which the wavelengths are shorter than the wavelengths of infrared light.

It is possible in one embodiment to design the light emitter as an emitter for only infrared light. The component configured as a light absorber is configured through the choice of the material for selective absorption of infrared light in such an embodiment.

The power range of the electric power consumption of the light emitter is preferably in the range of 1 W to 1,000 W and especially preferably in the range of 100 W to 600 W.

BRIEF DESCRIPTION OF THE FIGURES

Exemplary embodiments of the heat exchanger according to the present teaching are explained in greater detail below with reference to the figures. Additional details and advantages are described in greater detail on the basis of the exemplary embodiments illustrated in the figures. The reference numerals in the figures all have the same meanings in all figures.

DETAILED DESCRIPTION OF THE FIGURES

Figure 1:
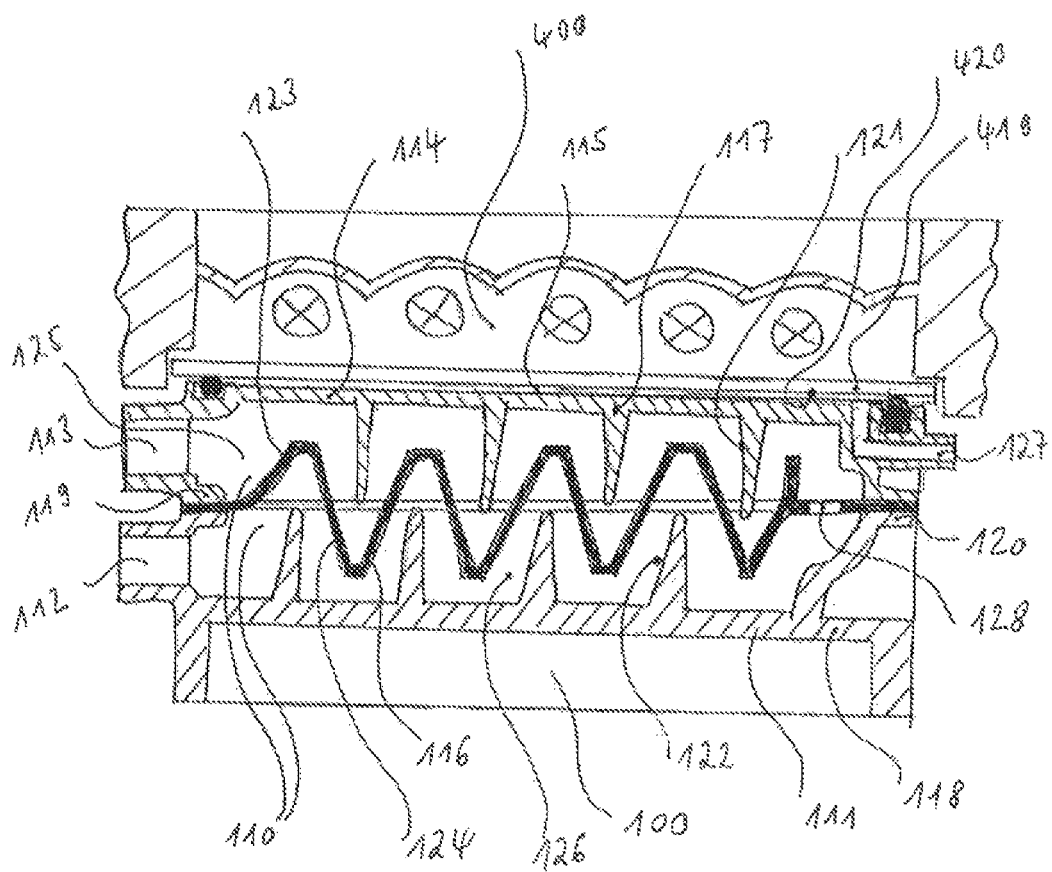
FIG. 1 shows a schematic sectional diagram of the arrangement of a heat exchanger on a light emitter.

FIG. 1 shows a schematic sectional diagram of the arrangement of a medical heat exchanger 100 on a light emitter 400. In this exemplary embodiment, the light emitter 400 is a component on the machine end of a medical fluid treatment device and the medical heat exchanger 100 is embodied as a disposable item.

The light emitter 400 has a plurality of incandescent bulbs represented by crosses in FIG. 1, arranged side by side to achieve the most uniform possible exposure of the passage 410 to the light emitter 400. The light-transmitting section 410 of the light emitter 400 in the present exemplary embodiment is a planar transparent pane of glass made of colorless glass. The side of the light-transmitting section 410 facing away from the incandescent bulbs forms a coupling surface 420, which is configured in its shape and dimensions for coupling the medical heat exchanger 100. Not shown in FIG. 1 are the devices for securing the heat exchanger 100 on the coupling surface 420. For example, clamping devices or doors are suitable for pressing and holding the medical heat exchanger for this purpose.

In the present exemplary embodiment, the medical heat exchanger 100 is constructed of a first housing part 117 with a first peripheral flange 119 and a second housing part 118 with a second peripheral flange 120, the two housing parts both being designed as shells. The first housing part 117 with its first peripheral flange 119 is connected to the second peripheral flange 120 of the second housing part 118 with a fluid-tight seal, the peripheral edge of the light absorber 116 being arranged as the seal between the flanges. The light absorber 116 is thus clamped between the housing part 117 and a housing part 118, subdividing the interior of the fluid chamber 110 into a first flow channel 125 facing the light-transmitting section of the fluid chamber 114 and a second flow channel 126 facing the light-transmitting section of the fluid chamber 114. The second flow channel 126 has an inlet in the outside wall 112 for supplying the medical fluid into the second flow channel 126. The first flow channel 125 has an outlet in the outside wall 113 for removing the medical fluid from the first flow channel 125. In the present exemplary embodiment, the inlet and the outlet are situated close together so that the flow channels 125, 126, connected in series, form on the whole a U-shaped fluid chamber in the cross section shown here, such that the flow channels 125, 126 are connected via a fluid-permeable opening 128 in the light absorber 116.

In the present exemplary embodiment, when the medical fluid flows through the medical heat exchanger, then the medical fluid first heats up in the colder second flow channel 126 which faces away from the light-transmitting section of the fluid chamber 114 and then faces the fluid chamber 114 with the light-transmitting section in the first flow channel 125, which is warmer. This permits an especially efficient heat transfer.

The first housing part 117 is formed in a section of the light-transmitting section of the fluid chamber 114. The material of the outside wall Is designed to be flat and transparent at least in this area and is also configured through its shape and dimensions for the coupling of the medical heat exchanger 100 to the coupling surface of the light emitter 420, so that light from the light-transmitting section in the light emitter 410 can radiate into the light-transmitting section in the fluid chamber 114.

In the present exemplary embodiment, the medical heat exchanger has a reinforcement in the form of a peripheral web on the outside of the second housing part 118, so that the medical heat exchanger has a high rigidity on the whole. In the present exemplary embodiment, air can be sucked through a suction channel 127 out of the interspace between the light-transmitting section in the fluid chamber 114 and the light-transmitting section in the light emitter 410 to minimize the absorption of light in the interspace and to ensure an especially secure coupling of the heat exchanger. However in other embodiments the suction channel 127 may be omitted.

The passage in the light emitter 410 and the light-transmitting section in the fluid chamber 114 absorb only a small portion of the of the Incident power in the case of incident light and allow most of the incident power to enter the fluid chamber 110. Most of the incident power is absorbed by the light absorber 116 in the fluid chamber, so that the light absorber 116 heats up.

When the medical heat exchanger is coupled to the light emitter 400 and medical fluid flows through it, and the light emitter 400 which is in operation emits light, then the light absorber emits its absorbed heat through thermal conduction and infrared radiation to the medical fluid, thereby gently heating the medical fluid.

Figure 2:
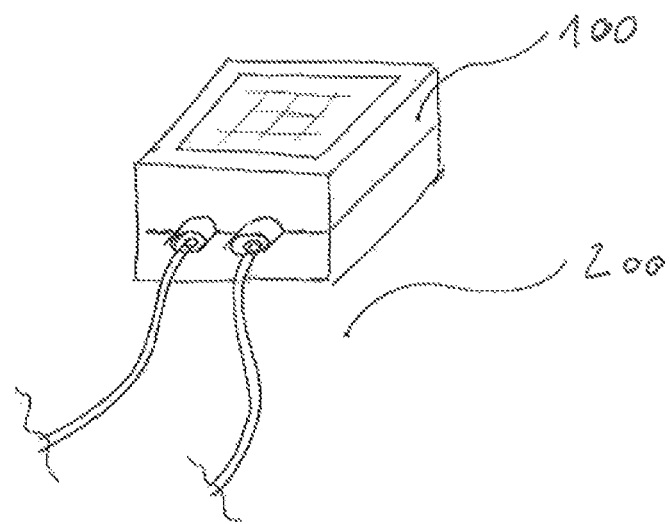
FIG. 2 shows a schematic diagram of a medical tubing set having an integrated medical heat exchanger.

FIG. 2 shows an embodiment of the heat exchanger from FIG. 1, where the heat exchanger 100 is integrated into a medical tubing set 200. The medical tubing set is indicated in FIG. 2 merely schematically by a supplying line and a discharge line on the medical heat exchanger 100. It is obvious for those skilled in the art that the medical tubing set 200 may also have known additional components besides the medical heat exchanger and the aforementioned tubing lines. Such known additional components may include, for example, the usual components of a blood tubing set for the extracorporeal blood treatment or of a medical tubing set from the field of infusion technology such as, for example, connectors, pump tubing segment for connecting a rolling pump, dialyzer, air bubble separator, drip chamber, clot catcher, hose clamps, measuring cells, and injection sites.

The medical tubing set 200 can be sterilized and packaged together with the associated medical heat exchanger in the manufacturing process, which amounts to an advantage for clinical use in handling.

Figure 3:
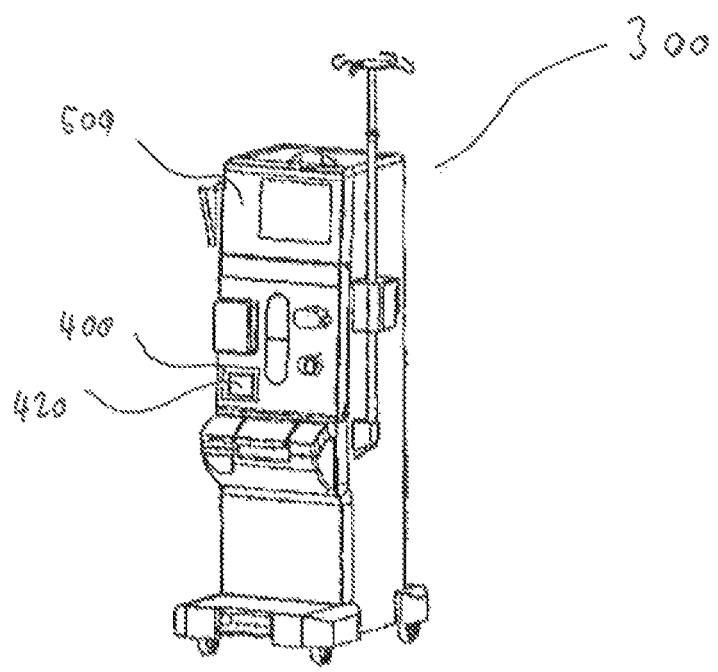
FIG. 3 shows a schematic diagram of a medical fluid treatment device having a coupling surface for coupling a medical heat exchanger.

FIG. 3 shows a schematic diagram of a medical fluid treatment machine 300 having a light emitter 400 and a coupling area for the light emitter 420, which is configured for coupling a heat exchanger 100 as a component of the medical tubing set 200 from FIG. 2. This does not show the known devices in medical fluid treatment machines for conveying the medical fluid in the medical tubing set 200, namely, in the present exemplary embodiment, a roller pump (not shown in FIG. 3), into which the pump tubing segment of the medical tubing set is inserted. This also does not show the device for measuring the temperature on a medical tubing set 200, which is known with medical fluid treatment machines, namely in the present exemplary embodiment, as a measurement pickup for a tubing segment of the medical tubing set and arranged downstream from the outlet of the medical heat exchanger 200.

The medical fluid treatment machine 300 has a control and/or regulating unit 500 having a controller, which has a signal connection to the device for measuring the temperature on the medical tubing set 200 downstream from the medical heat exchanger 200. Furthermore, the control and/or regulating unit 500 has a signal connection with the light emitter. In addition, the control and/or regulating unit 500 has an input unit for manual input of a numerical value of a setpoint temperature.

A computer program having program code, which regulates the power of the light emitter, is stored in the controller of the control and/or regulating unit 500, so that the predetermined setpoint temperature is maintained within predetermined limits when the program code is running in the control and/or regulating unit 500.

| List of reference numerals | |
|---|---|
| Reference numeral | Name |
| 100 | medical heat exchanger |
| 110 | fluid chamber |
| 111 | outside wall |
| 112 | inlet in the outside wall |
| 113 | outlet in the outside wall |
| 114 | light-transmitting section in the fluid chamber |
| 115 | coupling surface of the heat exchanger |
| 116 | light absorber |
| 117 | first housing part |
| 118 | second housing part |
| 119 | first peripheral flange |
| 120 | second peripheral flange |
| 121 | three-dimensional structure of the first housing part |
| 122 | three-dimensional structure of the second housing part |
| 123 | first three-dimensional area of the absorber |
| 124 | second three-dimensional area of the absorber |
| 125 | first flow channel |
| 126 | second flow channel |
| 127 | suction channel |
| 128 | fluid-permeable opening |
| 200 | medical tubing set |
| 300 | medical fluid treatment device |
| 400 | light emitter |
| 410 | light-transmitting section |
| 420 | coupling surface |
| 500 | control and/or regulating unit |

The invention claimed is:

1. A medical heat exchanger, for heating a medical fluid by light, comprising
at least one fluid chamber configured to receive and conduct the medical fluid, having at least one outside wall forming a fluid-tight fluid chamber,
at least one inlet in the outside wall of the fluid chamber for supplying the medical fluid into the fluid chamber and at least one outlet in the outside wall of the fluid chamber for removing the at least one medical fluid from the fluid chamber, and
at least one section of the outside wall of the fluid chamber configured as a light-transmitting section,
wherein the medical heat exchanger has at least one component configured as a light absorber subdividing the fluid chamber into first and second flow channels such that there is direct contact between the medical fluid and the component configured as a light absorber by flow of the medical fluid through the first and second flow channels when the medical fluid is in the fluid chamber.

2. The medical heat exchanger according to claim 1, wherein the section of the outside wall of the fluid chamber which is configured as a light-transmitting section essentially forms a planar surface or a curved surface.

3. The medical heat exchanger according to claim 1, wherein the medical heat exchanger is designed as a transparent plastic injection-molded part in at least some sections.

4. The medical heat exchanger according to claim 1, wherein at least the section of the outside wall of the fluid chamber which is configured as a light-transmitting section is transparent.

5. The medical heat exchanger according to claim 1 further comprising
a first housing part having a first peripheral flange and a first surface facing the interior of the fluid chamber and
a second housing part having a second peripheral flange and a second surface facing the interior of the fluid chamber,
such that the first peripheral flange is connected to the second peripheral flange with a fluid-tight seal.

6. The medical heat exchanger according to claim 5, wherein the component configured as a light absorber is held between the first peripheral flange and the second peripheral flange and extends into the fluid chamber.

7. The medical heat exchanger according to claim 5, wherein at least one of the first housing part first surface and the second housing part second surface has a three-dimensional structure in at least some sections of the surface.

8. The medical heat exchanger according to claim 5, wherein the component configured as a light absorber has at least one of
a first surface forming a substantially closed first three-dimensional area and
a second surface forming a substantially closed second three-dimensional area.

9. The medical heat exchanger according to claim 8, wherein
the first surface of the first housing part and the first surface of the component configured as a light absorber form a first flow channel for the at least one medical fluid and
the second surface of the second housing part and the second surface of the component configured as a light absorber form a second flow channel for the at least one medical fluid, such that the first flow channel develops into the second flow channel in order to carry the medical fluid.

10. The medical heat exchanger according to claim 9, wherein the first flow channel has the at least one inlet for supplying the at least medical fluid, and the second flow channel has the at least one outlet for removing the at least one medical fluid.

11. The medical heat exchanger according to claim 9, characterized in that at least one of
- the first flow channel is designed with a meandering shape following the substantially closed first three-dimensional area of the first surface of the first housing part and following the first surface of the component configured as a light absorber and
- the second flow channel is designed with a meandering shape following the substantially closed second three-dimensional area of the second surface of the second housing part and following the second surface of the component configured as a light absorber.

12. The medical heat exchanger according to claim 1, wherein the component configured as a light absorber is made of a compounded material, an injection-molded part coated by metal vapor, an extrusion part coated by a metal vapor, a metal, or a ceramic material.

13. The medical heat exchanger according to claim 1, wherein the section of the outside wall of the fluid chamber configured as a light-transmitting section is made of a material selected from the group consisting of glass, quartz glass, polypropylene (PP), and polycarbonate (PC).

14. The medical heat exchanger according to claim 1 designed as a disposable medical article.

15. A medical tubing set having at least one medical heat exchanger according to claim 1, wherein at least one of
- the at least one inlet in the outside wall of the fluid chamber for supplying the at least one medical fluid to the fluid chamber is connected to a tubing line of the medical tubing set and
- the at least one outlet in the outside wall of the fluid chamber for removing the at least one medical fluid from the fluid chamber is connected to a tubing line of the medical tubing set.

16. A medical fluid treatment device having at least one light emitter and at least one medical heat exchanger according to claim 1.

17. A medical fluid treatment device having at least one light emitter and at least one medical heat exchanger according to claim 1, wherein the light-transmitting section of the at least one medical heat exchanger is configured as a coupling surface.

18. The medical fluid treatment device according to claim 16, wherein the light emitter is configured as an emitter for selectively emitting a spectrum of light in which the wavelengths are shorter than the wavelengths of infrared light.

19. The medical fluid treatment device according to claim 16 designed as an extracorporeal blood treatment machine.

20. The medical fluid treatment device according to claim 16 designed as an infusion device or an infusion machine.

21. The medical fluid treatment device according to claim 17 further having a medical tubing set, wherein one or both of the at least one inlet in the outside wall of the fluid chamber is connected to a tubing line of the medical tubing set and the at least one outlet in the outside wall of the fluid chamber is connected to a tubing line of the medical tubing set.

22. The medical heat exchanger according to claim 12, wherein the compounded material is selected from the group consisting of a compounded injectable thermoplastic material and a compounded extrudable thermoplastic material, wherein the metal is stainless steel, and wherein the ceramic material is $Al_2O_3$ or AlN.

23. The medical heat exchanger according to claim 1 designed as a disposable medical fluid cassette.

24. The medical fluid treatment device according to claim 16 designed as an extracorporeal blood treatment machine selected from the group consisting of a peritoneal dialysis machine, a hemodialysis machine, a hemofiltration machine, a hemodiafiltration machine, and an apheresis machine.

* * * * *